(12) United States Patent
Heisel

(10) Patent No.: US 9,067,166 B2
(45) Date of Patent: Jun. 30, 2015

(54) PROCESS FOR THE REMOVAL OF HYDROGEN SULFIDE FROM A GAS STREAM

(71) Applicant: ITS Reaktortechnik GmbH, Pullach (DE)

(72) Inventor: Michael Heisel, Pullach (DE)

(73) Assignee: ITS Reaktortechnik GmbH, Pullach (DE)

(*) Notice: Subject to any disclaimer, the term of this patent is extended or adjusted under 35 U.S.C. 154(b) by 357 days.

(21) Appl. No.: 13/681,484

(22) Filed: Nov. 20, 2012

(65) Prior Publication Data

US 2013/0129589 A1    May 23, 2013

(30) Foreign Application Priority Data

Nov. 21, 2011  (EP) .................................... 11189978

(51) Int. Cl.
*B01D 53/00* (2006.01)
*C01B 3/58* (2006.01)
*C07C 7/17* (2006.01)
*B01D 53/86* (2006.01)
*C10L 3/10* (2006.01)
*C01B 17/04* (2006.01)

(52) U.S. Cl.
CPC ............. *B01D 53/002* (2013.01); *C01B 3/58* (2013.01); *C07C 7/17* (2013.01); *C01B 17/0404* (2013.01); *B01D 53/8612* (2013.01); *B01D 53/869* (2013.01); *C01B 17/0469* (2013.01); *B01D 2251/102* (2013.01); *B01D 2251/11* (2013.01); *B01D 2255/20707* (2013.01); *B01D 2255/20746* (2013.01); *B01D 2255/20753* (2013.01); *B01D 2255/20769* (2013.01); *B01D 2255/2092* (2013.01); *B01D 2256/24* (2013.01);
*B01D 2258/05* (2013.01); *C01B 2203/045* (2013.01); *C01B 2203/0485* (2013.01); *C10L 3/103* (2013.01)

(58) Field of Classification Search
None
See application file for complete search history.

(56) References Cited

U.S. PATENT DOCUMENTS

| | | | | |
|---|---|---|---|---|
| 2,785,056 | A * | 3/1957 | Thumm et al. | 423/570 |
| 5,676,921 | A * | 10/1997 | Heisel et al. | 423/573.1 |
| 7,226,572 | B1 * | 6/2007 | Keller et al. | 423/573.1 |
| 2002/0159938 | A1 * | 10/2002 | Fenderson | 423/230 |
| 2005/0158217 | A1 * | 7/2005 | Olbert et al. | 422/109 |

(Continued)

FOREIGN PATENT DOCUMENTS

| | | | |
|---|---|---|---|
| DE | 3526706 | * | 1/1987 |
| DE | 100 64 008 A1 | | 7/2002 |

(Continued)

OTHER PUBLICATIONS

Michael Heisel et al., "Clinsulf-Do zur Schwefelruckgewinnung aus H2S-Haltigem Gas," Berichte Aus Technik und Wissenschaft, vol. 70, pp. 15-19 (1993).

(Continued)

*Primary Examiner* — Melvin C Mayes
*Assistant Examiner* — Sheng H Davis
(74) *Attorney, Agent, or Firm* — Phan Law Group PLLC

(57) ABSTRACT

The application relates to a process for the removal of hydrogen sulfide from a gas stream by catalytic direct oxidation without employing the combustion step of a Claus process. The process is particularly suitable for desulfurization of gas streams that contain hydrogen and allows sulfur recovery efficiency of better than 99%.

14 Claims, 5 Drawing Sheets

(56) References Cited

U.S. PATENT DOCUMENTS

2006/0067875 A1* 3/2006 Koss et al. ............... 423/573.1
2007/0134147 A1* 6/2007 Graville ................... 423/242.1

FOREIGN PATENT DOCUMENTS

| DE | 10 2010 004 070 A1 | | 7/2011 |
| DE | 102010034070 | * | 2/2012 |
| EP | 0 283 793 A1 | | 9/1988 |
| EP | 1 555 241 A1 | | 7/2005 |
| EP | 1 621 250 A1 | | 2/2006 |

OTHER PUBLICATIONS

Extended European Search Report issued in EP Patent Appl. No. 11 189 978.7-2113.

* cited by examiner

PROCESS FOR THE REMOVAL OF HYDROGEN SULFIDE FROM A GAS STREAM

PRIORITY CLAIM

This application claims the right of priority under 35 U.S.C. §119(a) to European Patent Application No. 11189978 filed on 21 Nov. 2011; the entire content of which is hereby incorporated by reference.

FIELD OF THE INVENTION

The present invention relates to a process for the removal of hydrogen sulfide and sulfur recovery from a gas stream by catalytic direct oxidation without employing the combustion step of a Claus process. The process is particularly suitable for desulfurization of gas streams that contain hydrogen.

BACKGROUND OF THE INVENTION

The presence of sulfur in industrial gases causes significant environmental problems, and therefore, strict requirements are in place to remove sulfur from gas streams, in particular in petroleum refinery and natural gas plants but also in biogas plants, from $H_2S$ scrubbers, etc. A widespread method for desulfurization of sulfur-containing gas streams, in particular from gas streams in petroleum refineries and natural gas plants is the Claus process. The Claus process is long-known and operates in two major process steps. The first process step is carried out by a so-called Claus furnace. In this process step hydrogen sulfide is converted to elemental sulfur and sulfur dioxide at temperatures of approximately 1100 to 1300° C. by the combustion of about one third of the hydrogen sulfide in the gas stream. The so obtained sulfur dioxide reacts with hydrogen sulfide in the furnace to elemental sulfur. Thus, in this first step of the Claus process ca 60 to 70% of the $H_2S$ in the feed gas are converted.

To achieve higher sulfur recovery rates two to three catalytic steps follow where the Claus reaction

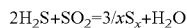

continues. From these steps a gas mixture results which is called the Claus tail gas. The Claus tail gas is usually subjected to further treatment in order to reduce the sulfur content of the gas to an even higher degree. For such further treatment of the Claus tail gas several methods are known, e.g. the subdew point methods, the recycle methods and the direct oxidation methods.

A recent development for the catalytic treatment of the gas mixture obtained in a Claus furnace is the so called "Clinsulf®" process. An overview over the Claus process using the Clinsulf process is provided in the article by M. Heisel and F. Marold in "Linde, Berichte aus Technik and Wissenschaft, 62/1988, pages 33 to 38". The Clinsulf process is a catalytic process using an internally cooled reactor which is constructed in two sections. The inlet section contains a non-cooled adiabatic bed which allows the reaction temperature to rise quickly and thus increase the speed of reaction. The second section of this reactor comprises a catalytic bed containing a coiled heat exchanger which provides efficient cooling enabling the reactor outlet temperature to be lowered close to the sulfur dew point.

The Clinsulf process has also been adapted to work as a direct oxidation process by introducing an oxygen containing gas into the Clinsulf reactor. This process is mainly used to treat Claus tail gas but it has also been suggested e.g. for biogas desulfurization without the use of a Claus furnace, and here it can be referred e.g. to the article of M. P. Heisel, F. J. Marold and M. Gwinner in "Linde, Reports on Science and Technology, 53/1994, pages 15 to 19".

The known Clinsulf® reactors contain coiled heat exchangers in the second section of the reactor. This is disadvantageous because such heat exchangers are difficult to manufacture and are thus very expensive. This has prevented so far a wide use of the Clinsulf® process but in particular of the Clinsulf DO® process which is the application of Clinsulf® as a Claus tailgas treatment or in biogas desulfurization. Clinsulf® DO was considered as being (economically) inferior to other processes such as the liquid redox process.

An improvement of the Clinsulf process but not of the Clinsulf DO process is the Clinsulf process using two "Clinsulf" reactors, i.e. two reactors having the inlet section with a non-cooled adiabatic bed and a second section with a cooled catalytic bed. The Clinsulf process and the Clinsulf reactor are also disclosed e.g. in DE 44 09 203. Other recent methods for desulfurization of gases essentially using the Claus process are disclosed e.g. in WO 2010/040495 or WO 2011/005638.

While the Claus process is very widely used in industry, there are several situations where the Claus process is not a suitable option. First of all, a Claus process requires a significant investment and is generally designed to process significant amounts of sulfur-containing gas. For small operations, e.g. small natural gas sources, the installation of a Claus process is usually not economical. Furthermore, the Claus process cannot be used for the desulfurization of gases from chemical plants, such as the desulfurization of hydrogen gas that has been used for the hydrogenation of sulfur-containing gases and is thus contaminated by hydrogen sulfide. Such gases cannot be desulfurized by the Claus process, because such gases would react, essentially be burned in the Claus furnace. The Clinsulf DO process with one reactor has been suggested for the desulfurization of biogas, but it was generally accepted that this process could not be used with gases containing hydrogen, because the hydrogen was believed to react with the catalyst contained in the direct oxidation reactor. The Clinsulf process using two reactors was thus never proposed for anything but as part of the Claus process using a Claus furnace.

For the desulfurization of lean $H_2S$ gases (i.e. gases which do not result in a stable flame in a Claus furnace) other methods are used in industry, such as a liquid redox process. In this process hydrogen sulfide is oxidized in an aqueous system at a temperature of about 50° C. using a suitable catalyst, generally a chelated iron catalyst. While the liquid redox process is very efficient in purification of gases containing hydrogen sulfide, the operational availability of this method is usually not higher than about 80% per year, because blocking of parts of the apparatus and ducts is inherent to the system. This results from the fact that three phases are necessarily prevalent in the system: The feed gas and the oxidation air are gaseous, the solvent is liquid, the sulfur produced solid. Further problems are foaming which requires the use of anti-foam agents. Anti-foam agents in the wash solution optimized for foam reduction in the re-oxidation vessel lead to foaming at other stages of the process, e.g. the scrubbing tower. Another problem is that the sulfur obtained with the liquid redox process is very often discolored, sometimes even black. Discolored sulfur cannot be sold so that revenues from the process are low or even negative because the sulfur obtained has to be disposed off, which costs additional money. Furthermore, the process is quite expensive due to chemical consumption in particular of the chelating agent.

Thus, there is a need in industry for a reliable process with a high operational availability and cheap in operation that can be used for the desulfurization of gases, where a Claus process is not economical or cannot be used for technical or chemical reasons. The process should provide a very high desulfurization efficiency of more than 99%.

SUMMARY OF THE INVENTION

This problem is solved by a process for the removal of hydrogen sulfide from a gas stream containing hydrogen sulfide by catalytic direct oxidation, which process comprises
a) mixing a gas stream containing hydrogen sulfide with an oxygen containing gas to obtain a gas stream containing both hydrogen sulfide and oxygen,
b) transferring the gas stream containing both hydrogen sulfide and oxygen into a first section of a first reactor, which first section contains a non-cooled adiabatic bed containing a first catalyst which catalyzes the oxidation of hydrogen sulfide with oxygen and the oxidation of hydrogen sulfide with sulfur dioxide, wherein the temperature of the adiabatic bed is $T_1$,
c) transferring the gas stream from the first section of the first reactor to a second section of the first reactor, which second section contains a second catalyst which is different from the first catalyst and which second section is kept at a temperature $T_2$ wherein $T_2 \leq T_1$ and $T_2$ is higher than the dew point temperature of elemental sulfur and not higher than 300° C. whereby a gas stream depleted in hydrogen sulfide is obtained,
d) transferring the gas stream depleted in hydrogen sulfide to a sulfur condenser to obtain a gas stream depleted in sulfur,
e) transferring the gas stream depleted in sulfur into the first section of a second reactor, which first section contains the same catalyst as the first section of the first reactor, wherein the first section of the second reactor is kept at a temperature that is above the dew point of the elemental sulfur so that in the first section of the second reactor no elemental sulfur precipitates as liquid or solid on the catalyst,
f) transferring the gas stream from the first section of the second reactor to the second section of the second reactor which contains the same catalyst as the second section of first reactor and which second section is kept at a temperature that is at or below the dew point of elemental sulfur so that in the second section of the second reactor elemental sulfur precipitates as liquid or solid on the catalyst,
g) removing the desulfurized gas stream from the second reactor and
h) after a defined time switching the operation conditions of the first reactor and the second reactor and switching the gas flow simultaneously so that the previous second reactor becomes the new first reactor and the previous first reactor becomes the new second reactor,
i) wherein the gas stream containing hydrogen sulfide that is introduced into the first reactor has not previously been subjected to the combustion step of a Claus process.

BRIEF DESCRIPTION OF THE DRAWINGS

In the following the present invention will be explained in more detail with reference to the figures.

DETAILED DESCRIPTION OF THE INVENTION

Figure 1:
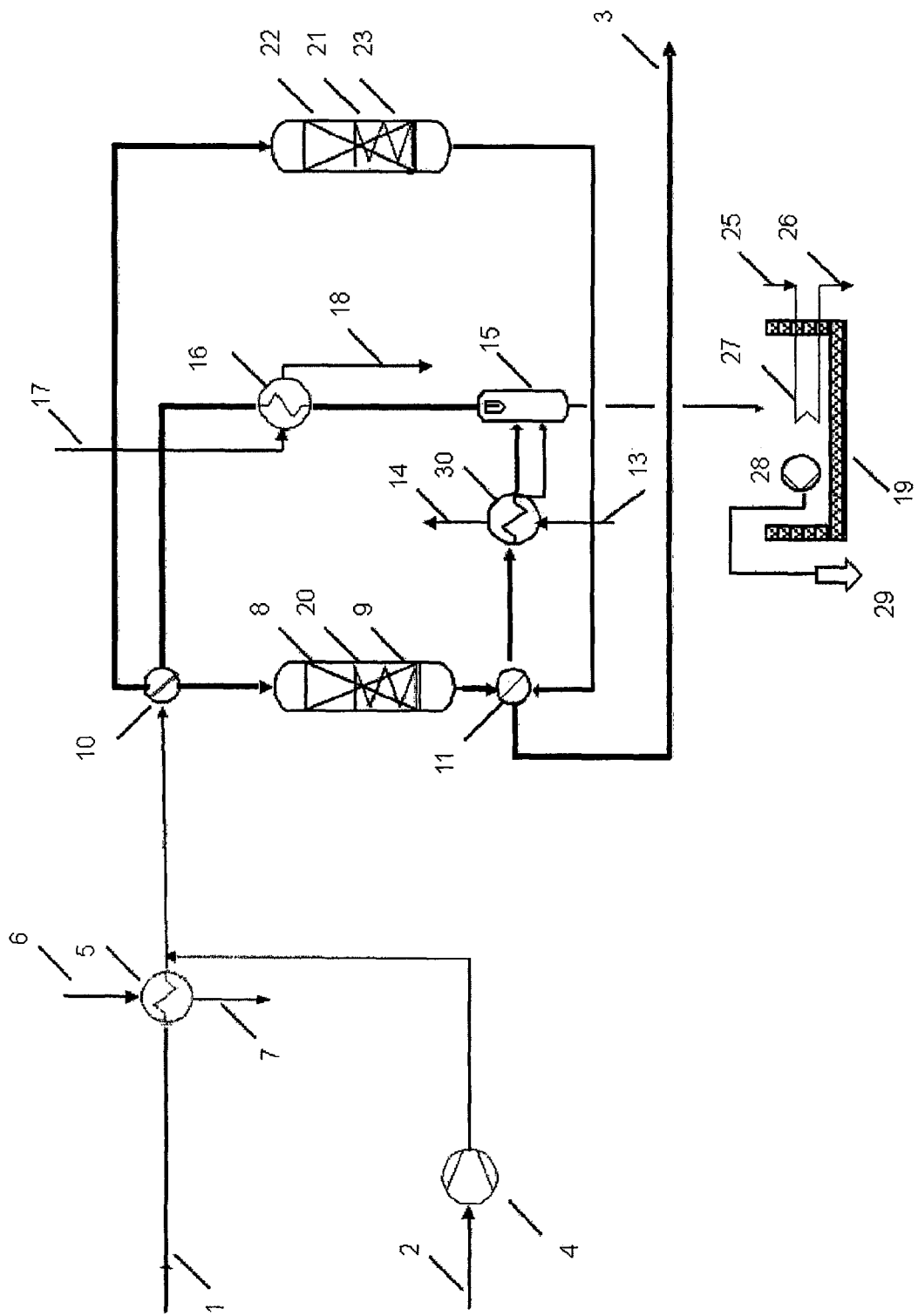
FIG. 1 schematically shows a preferred process of the present invention.

In this specification it is frequently referred to a "temperature in the first section" of a reactor or to a "temperature in the second section" of a reactor or a temperature that is kept at a certain value in a section of a reactor. It is to be understood that the gas entering a section of a reactor does not necessarily have the indicated temperature. Rather, the temperature in the first section of a reactor is defined as the temperature of the gas mixture leaving the first section of this reactor and the temperature in the second section of a reactor is defined as the temperature of the gas mixture leaving the second section of this reactor. The same applies if a certain temperature is "kept" in a section of a reactor. The temperature is usually taken immediately downstream from the corresponding section of the reactor and preferably as close as possible to the outlet of the section.

The inventor of the present invention found that a process that is similar to the Clinsulf process using two so-called "Clinsulf" reactors can be used for the direct oxidation of hydrogen sulfide-containing gases without using a complete Claus process and in particular without first subjecting the gas stream to a Claus furnace. The above process can also be used for the desulfurization of gases containing hydrogen and even for the desulfurization of gases consisting essentially of hydrogen. Unexpectedly, the hydrogen does react only to a negligible extent with oxygen or sulfur under the operation conditions, especially the temperatures used in the process of the present invention.

While in a conventional Claus process for which the Clinsulf process was developed in the Claus furnace most of the hydrogen sulfide is oxidized to sulfur and sulfur dioxide and in the later oxidation stage then the remaining hydrogen sulfide reacts with sulfur dioxide to sulfur and water, in the process of the present invention no Claus furnace is used. Rather, the gas-containing hydrogen sulfide is mixed with an oxygen-containing gas (such as air) and then transferred into the first section of a first reactor. This first section of the first reactor contains a catalyst bed and no heat exchanger and is operated as an adiabatic bed without cooling. Here the temperature is kept at a temperature $T_1$ which is usually not higher than 300° C., and at this temperature the hydrogen sulfide can react selectively with oxygen in the presence of the catalyst contained in the adiabatic bed. Preferably 180° C.$\leq T_1 \leq$300° C. Thus, contrary to a usual Claus process, where many side-reactions take place in the Claus furnace, in the process of the present invention the reaction

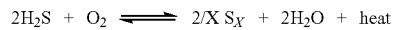

takes place very selectively.
X in this equation is 2, 4, 6, 7 or 8 and corresponds to the different modifications of elemental sulfur.

In this reaction a part of the hydrogen sulfide may be oxidized to sulfur dioxide as in the Claus furnace.

After the reaction took place in the adiabatic bed, the gas stream containing remaining hydrogen sulfide+elemental sulfur+water+sulfur dioxide is then transferred to the second section of the first reactor. In the second section of the first reactor a different catalyst is present than in the first section which catalyzes only the Claus reaction:

$$2H_2S + SO_2 = 3/xS_x + 2H_2O + heat \qquad \text{Eq. 1}$$

The second section of the first reactor contains means for heating or cooling the gas (a heat exchanger). The temperature of the second section of the first reactor is kept at a temperature $T_2$ which is not higher and preferably lower than $T_1$. $T_2$ is preferably below 300° C. but is higher than the dew point of the sulfur. In the second section of the first reactor the Claus Eq. 1 reaction:

$$2H_2S + SO_2 = 3/xS_x + 2H_2O + heat$$

occurs. This reaction is an equilibrium reaction, and the equilibrium is shifted to the side of the elemental sulfur the lower the temperature is. The temperature of the second section of the first reactor is kept above the dew point of the elemental sulfur, and thus, the equilibrium is not sufficiently shifted to the side of the elemental sulfur, but the sulfur is kept in gaseous form and thus does not contaminate the catalyst. This gas mixture containing the elemental sulfur but also the still minor amounts of hydrogen sulfide and sulfur dioxide is then passed to a sulfur condenser (a sulfur condenser is well-known in the art and used in all Claus processes; a standard sulfur condenser can be used according to the present invention), and in this sulfur condenser, as is known in the art, the temperature is lowered and elemental sulfur is recovered from the gas stream.

The gas stream so depleted in sulfur but still containing residual amounts of hydrogen sulfide and sulfur dioxide is then passed to the second reactor and there to the first section of the second reactor. The second reactor is identical to the first reactor, i.e. the second reactor also contains two sections, the first section is left adiabatic, the second section has means for heating and cooling the gas mixture (heat exchangers) and both sections contain a catalyst bed. However, the second section of the second reactor is operated at a temperature which is below the dew point of elemental sulfur, and the temperature can even be below the temperature at which sulfur becomes solid. It is necessary that both sections of the second reactor are operated at different temperatures, above the dew point in the first section, at or below the sulfur dew point in the second section. Operating the second section of the second reactor at such a low temperature has the advantage that the chemical equilibrium of the Claus reaction:

$$2H_2S + SO_2 \rightleftharpoons 3/X\, S_X + 2H_2O + heat$$

is shifted to the side of the elemental sulfur, thereby significantly reducing the remaining sulfur compounds and especially hydrogen sulfide. The "disadvantage" of operating the second reactor at such a low temperature is, of course, that the liquid or solid sulfur deposits on the catalyst and accumulates. Over time this leads to a deactivation of the catalyst. The gas leaving the second reactor is essentially free of hydrogen sulfide and can be further used or processed.

After some time of operation the catalyst of the second reactor is contaminated by liquid and/or solid elemental sulfur to such a degree that it can no longer sufficiently catalyze the reaction:

$$2H_2S + SO_2 \rightleftharpoons 3/X\, S_X + 2H_2O + heat.$$

At this stage of the process the operating conditions between the first reactor and the second reactor are switched, and the gas flow is also switched. Thus, now the first section of the previous second reactor is operated at the temperature $T_1$, and the second section of the previous second reactor is operated at the temperature $T_2$. The gas streams are also switched so that the gas stream to be desulfurized is now transferred to the first section of the previous second reactor. Accordingly, the previous first reactor is now operated at the temperatures of the previous second reactor and thus acts in the same way as the previous second reactor. Essentially, by switching the operation conditions and the gas flow, the previous second reactor now becomes the first reactor, and the previous first reactor now becomes the second reactor. The elemental sulfur deposited on the catalyst in the previous second reactor is desorbed at the new temperatures of operation and leaves the previous second reactor essentially with the gas stream which is transferred to the sulfur condenser.

The switch is repeated when the catalyst in the "new" second reactor is inactivated by the deposited sulfur.

All elemental sulfur is recovered in step b) of the claimed process in the conventional sulfur condenser and has an excellent quality which is suitable for commercial purposes. Only one sulfur condenser is necessary for the whole process.

In the process of the present invention principally known catalysts can be used that catalyze the Claus reaction:

$$2H_2S + SO_2 \rightleftharpoons 3/X\, S_X + 2H_2O + heat.$$

and the reaction $$2H_2S + O_2 \rightleftharpoons 2/X\, S_X + 2H_2O + heat$$

The first section of the first and second reactor contains a catalyst that catalyses both of the above reactions. Preferred is titanium dioxide as a catalyst, but other usual catalysts, in particular cobalt molybdenum or nickel molybdenum can also be used. A further suitable catalyst for the first section of the two reactors is iron, but better results are achieved with titanium dioxide, cobalt molybdenum and nickel molybdenum, in particular with titanium dioxide. Examples of suitable catalysts are the products "S 7001" of eurosupport (Amersfoort, The Netherlands) and "CRS 31" of the company AXENS (Paris, France). Other selective direct oxidation catalysts may also be used, as "Selectox" of Worley Parsons, or Superclaus of Jacobs Comprimo.

The second reaction of both reactors contains a selective Claus catalyst that only catalyses the reaction $$2H_2S + SO_2 \rightleftharpoons 3/X\, S_X + 2H_2O + heat.$$

Any known Claus catalyst, such as $Al_2O_3$ can be used. A typical commercial product would be CR3S from the company AXENS.

While it is principally possible to cool the reactors of the process of the present invention with heating and cooling coils, or also by straight tube or U-tube heat exchangers, preferably the heating and cooling of the second section of the two reactors used in the process of the present invention is effected by thermoplate technology. It is, of course, also possible to combine e.g. U-tube technology with thermoplate technology and use U-tubes in one reactor and thermoplates in another reactor. Preferably both reactors are identical and are tempered by the same system. Most preferably, the reactors are completely tempered by thermoplate technology.

Reactors with thermoplates are disclosed e.g. in DE 101 08 380, and the content of this application is included herein by reference regarding the description and use of thermoplates and reactors with such thermoplates. Thermoplate technology is also used in reactors disclosed e.g. in EP 1 621 250. In the reactors the thermoplates are usually combined to packages, and the packages are usually combined to modules. The catalyst is located between the thermoplates.

The thermoplates can be contained in the reactor horizontally or vertically. The height of the thermoplates is defined by the height of the catalyst in the second reaction of both reactors. In the reactors the thermoplates are preferably not completely adapted to the cylindrical reactor housing in order to obtain a more constant temperature of the cooling plates and thus a higher selectivity of the catalyst. Of course, it is possible to adapt the thermoplates completely to the wall of the reactor, however, this reduces the selectivity of the catalyst because it is very difficult to ensure equal flow of cooling medium, e.g. boiler feed water through plates of widely different sizing.

The switching process of the gases between the first and the second reactor can be done by usual and known distributors. Preferred devices for effecting the switching process are disclosed and described in DE 10 2010 034 070, the content of which is included herein by reference. A preferred distributor comprises a housing with at least a first, a second, a third and fourth opening and a barrier element, wherein at least two spaces are provided within the housing between the barrier element and the housing, and the barrier element can be rotated around an axis of rotation between a first position and a second position such that in the first and in the second position there is a fluid connection between at least two openings of the housing and one of the spaces such that one of the spaces provides a fluid connection between the two openings of the housing. In a particularly preferred embodiment of the present invention at least one of the spaces contains at least one leading element between the barrier element and the housing.

The temperature in the first section of the first reactor is sufficiently high to allow the catalytic reaction between hydrogen sulfide and oxygen, and this temperature is preferably at least 180° C. and not more than 300° C. The temperature should not be so high that the catalyst looses selectivity or may even be deactivated, and therefore, the highest possible temperature depends on the catalyst used. Preferably, the catalyst used in the process of the present invention is titanium dioxide which is deactivated only at very high temperatures and can be used at temperatures of up to 400° C. and for limited time even above 400° C. However, even titanium dioxide significantly looses selectivity above 300° C. Preferably, the temperature in the first section of the first reactor is from 180 to 300° C., more preferred between 190 and 260° C.

The temperature in the second section of the first reactor is not higher and preferably lower than in the first section. It is advantageous that the temperature is as low as possible in order to shift the chemical equilibrium of the Claus reaction.

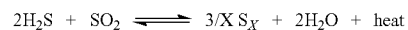

in the direction of elemental sulfur. However, in order to avoid deposition of sulfur on the catalyst and thus deactivation of the catalyst, the temperature is above the dew point of elemental sulfur. The dew point of elemental sulfur is dependent on the concentration of the elemental sulfur in the gas, and the temperature in the second section of the first reactor is preferably only slightly above the sulfur dew point. Preferably, the temperature in the second section of the first reactor is below 240° C. Most preferably, the temperature in the second section of the first reactor is in the range of 10° C. to 20° C. above the sulfur dew point.

The temperature in the first section and the second section of the second reactor must be different. For fast reaction the temperature in the first section should be 160 to 260° C., preferably 180 to 220° C. In order to shift the equilibrium of the Claus reaction as indicated above to the side of elemental sulfur, the temperature in the second section should be as low as possible and at or below the dew point of the elemental sulfur. However, it must be considered that at lower temperatures the reaction speed decreases (as a rule of thumb decreasing the temperature by 10° C. halves the reaction speed), and furthermore, the temperature must be above the dew point of water which in the process gas is typically in the range of 50° C. to 75° C. The dew point of the elemental sulfur decreases with the sulfur concentration in the gas. Since sulfur is adsorbed in the second section of the second reactor, the dew point of sulfur is lowered during the passage of the gas through the second section of the second reactor. Considering that at the outlet of the second section of the second reactor the concentration of sulfur is very low, at that part of the second reactor the dew point of elemental sulfur is about 125° C. Thus, preferably the temperature in the second section of the second reactor usually is in the range between 80 and 125° C., preferably in the range of 90 to 120° C.

The process of the present invention is particularly suitable in all situations where a Claus process is not economically advantageous or cannot be used for technical reasons. A typical situation in which the process of the present application can be used is the desulfurization of natural gas from small natural gas sources in which a complete Claus process would not be economical. Furthermore, the process can advantageously be used for the desulfurization of biogas and other hydrocarbon containing gases, since hydrocarbons do not react over the proposed catalysts for H2S oxidation, as they would do in a Claus furnace.

However, the process of the present application has been found to be particularly useful for the desulfurization of gases which contain hydrogen. It was believed in the prior art that the catalysts used for catalyzing the reaction:

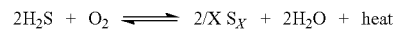

would facilitate the reaction of hydrogen with oxygen or sulfur. Therefore, a direct oxidation of a gas stream containing hydrogen gas for removing hydrogen sulfide was not considered possible in the art. Such gases cannot be subjected to the conventional Claus process either, because the hydrogen would be burned to form water vapor in the Claus furnace.

The inventors of the process of the present invention now surprisingly found that under the operation conditions of the process of the invention the catalysts in the two reactors do not catalyze the reaction of hydrogen to water or hydrogen sulfide and that therefore the claimed process can also be used for the desulfurization of hydrogen-containing gases, in particular of gases containing more than 10% hydrogen, preferred gases containing more than 30% hydrogen, more preferred of gases that contain 60% hydrogen or more, even more preferred of gases that contain 80% hydrogen or more such as 90% hydrogen or more, e.g. gas streams which consist essentially of hydrogen and usual contaminants such as the hydrogen sulfide that has to be removed.

Such hydrogen gases that contain hydrogen sulfide are produced e.g. in chemical plants, where sulfur is hydrogenated to hydrogen sulfide and the off-gas consists essentially of hydrogen but contains significant amounts of hydrogen sulfide as contaminants. It is necessary to remove the hydrogen sulfide from the off-gas and thus to purify the hydrogen gas for further use.

The process is preferably used in gases which contain besides hydrogen sulfide also hydrocarbons with up to six carbon atoms, (such as biogas which contains about 60 volume-% methane), unsaturated hydrocarbons in an amount of up to 1 volume-%, preferably of up to 0.1 volume-%, and hydrogen gas in an amount of up to 100 volume-%.

The process of the present invention is particularly suitable for the desulfurization of gas streams containing low concentration of hydrogen sulfide such as 4 volume-% of hydrogen sulfide or less, e.g. from 0.5 to 4 volume-% of hydrogen sulfide, preferably of 1 to 4 volume-% of hydrogen sulfide such as 1 to 3 volume-% of hydrogen sulfide. However, it is also possible to use the process of the present invention for desulfurization of gas streams containing higher amounts of hydrogen sulfide, e.g. from 3 volume-% to 100 volume-%, preferably from 3 volume-% to 15 volume-%. If the concentration of hydrogen sulfide in the gas stream to be purified is above 3 vol. %, preferably above 4 vol. % the temperatures in the reactors might be difficult to control. In this case it can be preferable to recycle a part of the product gas in order to reduce the temperature in the reactors. This technique will be described next.

As explained above, if the content of hydrogen sulfide in the gas that is to be desulfurized is too high, e.g. more than 3 volume-%, in particular 4 volume-% or more, high temperatures can occur which could would reduce selectivity and deactivate or destroy the catalyst and which are difficult to control. In such a situation it is preferred to recycle a part of the product gas into the gas mixture that enters the first reactor or to distribute oxygen-containing gas (in particular air) between the two reactors. Of course, it is also possible to combine the recycling of a part of the product gas and the addition of oxygen-containing gas to both reactors. With these measures the maximum temperature that can be reached in both reactors can be controlled.

In the above described embodiment in which part of the product gas is recycled into the gas mixture that enters the first reactor, the recycled gas has the function to dilute the gas mixture that enters the first reactor. By this dilution the concentration of the hydrogen sulfide is reduced and in consequence the temperature in the first section of the reactor is also reduced.

In the above described embodiment in which the oxygen containing gas is distributed between the first section of the first reactor and the first section of the second reactor, a part of the original hydrogen sulfide reacts with the oxygen in the first section of the first reactor and a part of the original hydrogen sulfide reacts with the oxygen in the first section of the second reactor. This also reduces the maximum temperature that can occur in the first section of each reactor.

In a preferred embodiment the thermoplates are horizontally arranged in the reactors used in the process of the present invention. With such a horizontal arrangement of the thermoplates all thermoplates can be exactly equal, which allows an efficient cooling of the thermoplates, and the cooling of each thermoplate is identical. This embodiment is preferred.

It is also possible to use a vertical arrangement of the thermoplates in the reactor, and the advantage of such a vertical arrangement is that the space of the (usual cylindrical) reactor can be optimally used. However, if the thermoplates are vertically arranged and adapted to the outer shape of the (cylindrical) reactor, the plates are not all equally sized and cooling of the plates is not equal, which leads to a lower selectivity of the reaction. It is also possible when using thermoplates which are vertically arranged not to completely adapt the thermoplates to the cylindrical wall of the reactor, which allows a more equal cooling of the thermoplates so that the surfaces of the thermoplates which transfer the heat of the reaction have essentially the same temperature.

With a vertical arrangement of thermoplates in the reactors wherein the thermoplates are (partially) adapted to the cylindrical shape of the reactors, it is preferred to use differently sized supply lines and discharge lines for the thermoplates so that the loss of pressure in the supply lines and the discharge lines of the thermoplates and during the passing of the cooling agent through the thermoplates in differently sized thermoplates is essentially the same.

Furthermore, it is preferred in the case of vertically arranged thermoplates that the cooling is improved by using thermoplates which have lateral weldings so that the cooling agent is directed within the thermoplates to increase the path length of the cooling agent in the thermoplates. This makes it possible to control the loss of pressure in differently sized thermoplates. Such thermoplates are disclosed e.g. in WO 2009/095221, e.g. in FIGS. 6 and 7 and this document is included herein by reference insofar as such thermoplates are disclosed.

The process of the present invention is preferably used for the desulfurization of gas streams having an increased pressure, e.g. for the natural gas from small gas sources, where the desulfurization should be carried out directly at the gas source. In fact, with an increased pressure the efficiency of the desulfurization is increased. At increased pressure the temperatures must of course be adjusted, because the dew point of sulfur depends on the pressure of the gas. The process of the present invention is particularly suitable for the desulfurization of gas streams having a pressure in the range of 1 bara to 70 bara, preferably of 2 bara to 20 bara (bara=bar absolute).

The process shown in FIG. 1 is particularly suitable, if the gas stream which should be desulfurized contains low amounts of hydrogen sulfide such as 3 volume-% of hydrogen sulfide or below.

The gas stream 1 that is to be desulfurized, e.g. biogas, is transferred to device 5 for pre-heating the gas stream. The device 5 is heated by a heating agent which enters at 6 and leaves at 7. After pre-heating the gas stream, it is mixed with an oxygen-containing gas 2 such as air, which has been compressed in the compressor 4. The gas stream containing the hydrogen sulfide and the oxygen is then transferred to the distributor 10 which leads the gas stream to the first section 8 of the first reactor 20 which contains a catalyst and is operated as an adiabatic bed without cooling. From the first section 8 of the first reactor 20 the gas stream passes to the second section 9 of the first reactor 20 which also contains a catalyst and a heat exchanger, and here the reaction is controlled above the dew point temperature of elemental sulfur. From the second section 9 of the first reactor 20 the gas stream is led to the distributor 11 and from the distributor 11 to the sulfur condenser and separator 30 (which is cooled by a cooling agent entering at 13 and leaving at 14) and sulfur separator 15 which works together with the sulfur pit 19. The sulfur pit 19 contains a sulfur pit heating device 27 with lines 25 and 26 for heating the sulfur pit heating device 27. The sulfur pit 19 further contains a sulfur loading pump 28, and the clean sulfur is obtained at 29. The gas depleted in sulfur is then led from the sulfur separator 15 to the heating device 16 which is fed by heating fluid 17 which leaves at 18, and here the gas is again heated. From the heating device 16 the gas stream is then led to the distributor 10 and via distributor 10 to the first section 22 of the second reactor 21 and from here to the second section 23 of the second reactor 21 which are essentially identical to the corresponding sections of the first reactor 20 but which are operated at lower temperatures (below the dew point of the elemental sulfur in the cooled second section). The heating and cooling devices of the reactors 20 and 21 are not shown in FIG. 1.

From the second section 23 of the second reactor 21 the gas stream is then again led to distributor 11 and from distributor 11 to the exit 3 where the purified gas, e.g. the purified biogas, is collected.

After a defined time (when so much sulfur has been deposited on the catalyst in the second section of the second reactor that the catalytic activity decreases to a non-acceptable degree), the operating conditions (temperature profile) of the first reactor 20 and the second reactor 21 are switched. Furthermore, the distributors 10 and 11 are switched so that the incoming gas stream containing the non-purified gas that reaches distributor 10 is now first led to the second reactor 21, the gas exiting the second reactor 21 is then led via distributor 11 to the sulfur-separating devices 30 and 15, the pre-heating device 16 and distributor 10 to the first reactor 20, and after leaving the first reactor 20, the gas is led through distributor 11 and via distributor 11 to the exit 3 of the process.

Figure 2:
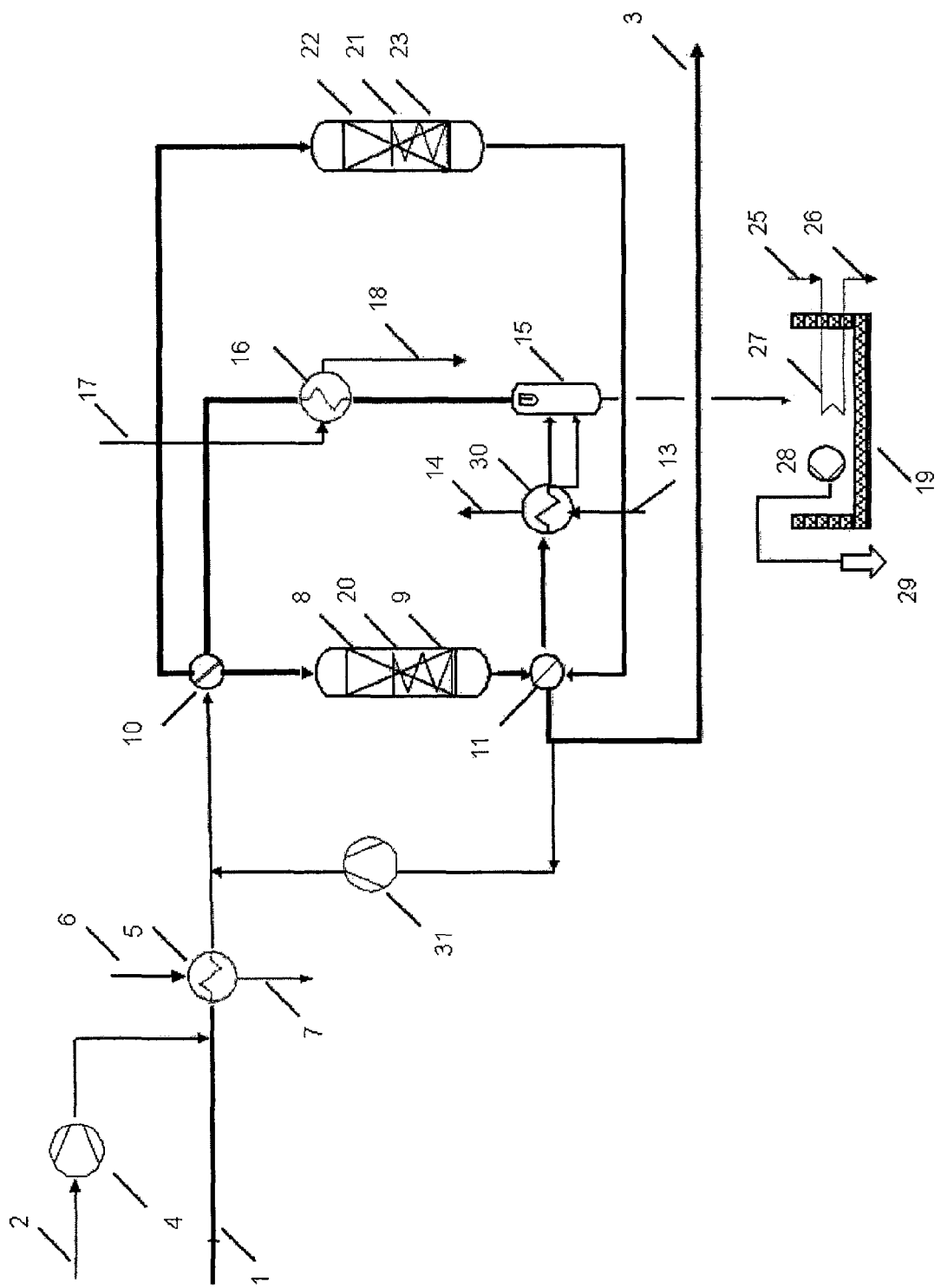
FIG. 2 also shows a preferred process of the present invention, which is particularly useful for desulfurization of gases containing high amounts of hydrogen sulfide.

The device shown in FIG. 2 essentially corresponds to the device shown in FIG. 1, however, the device shown in FIG. 2 is particularly suitable for the desulfurization of gas streams containing high amounts of hydrogen sulfide such as more than 3 volume-% of hydrogen sulfide. In the process shown in FIG. 2 the important difference to the process of FIG. 1 is the presence of the gas blower 31 which compresses some of the process gas and combines this compressed process gas as recycle gas with the gas stream incoming at 1.

This leads to better temperature control, in particular of the first section 8 of the first reactor 20. In essence by recycling a part of the product gas into the process, the concentration of hydrogen sulfide in the incoming gas is reduced. In addition, the temperature of the incoming gas stream is reduced. Heating device 5 can also act as cooling device if the incoming gas stream is too hot.

Figure 3:
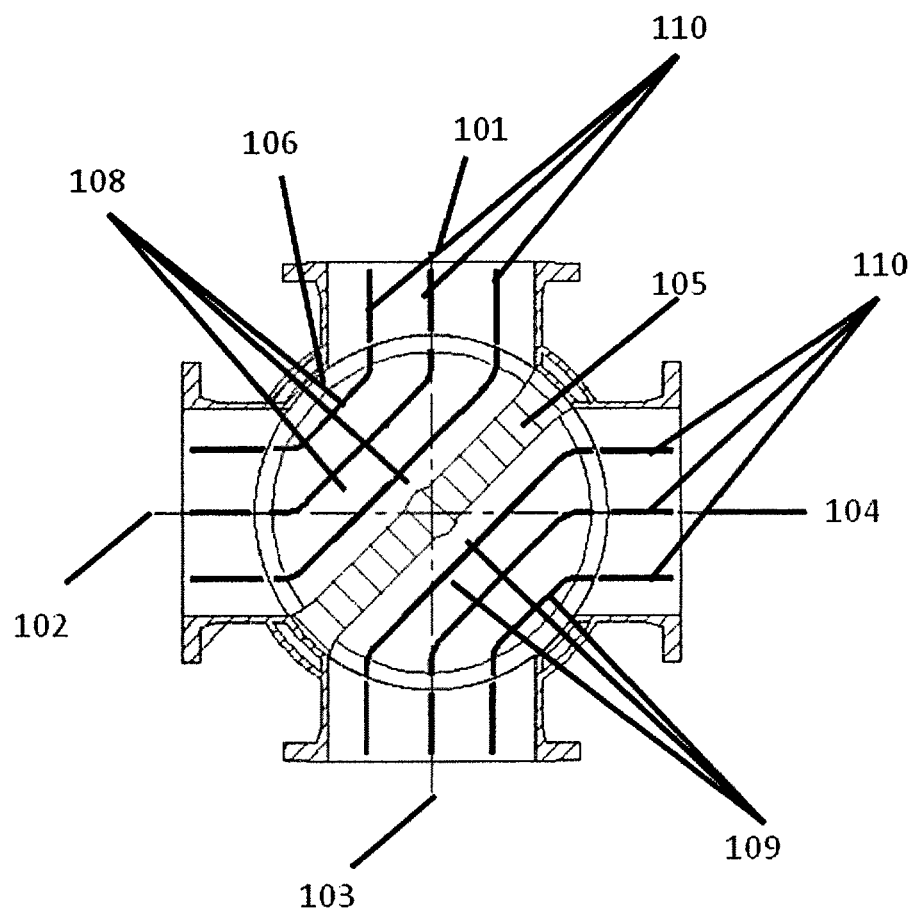
FIG. 3 shows a preferred distributor for use in the process of the present invention.

FIG. 3 shows a preferred distributor 10 and 11 for use in the process of the invention. The distributor contains four openings 101, 102, 103 and 104, a barrier element 105 and a housing 106 so that the barrier element 105 and the housing 106 define two spaces 108 and 109. Each of those two spaces connects two of the four openings. With the position of the barrier element 105 shown in FIG. 3 opening 102 is connected via the space 108 with opening 101, and opening 103 is connected via the space 109 with opening 104. If the distributor is switched, i.e. the barrier element is turned by 90°, the space 108 connects opening 102 with opening 103, and the space 109 connects opening 101 with opening 104. In the particularly preferred embodiment shown in FIG. 3 the distributor also contains leading elements 110. The presence of these leading elements reduces dead space and in particular reduces the fluid resistance of the distributor. This distributor combines the advantages of workability independent of temperature, a high operational availability and minimized dead space and a low loss in pressure.

Figure 4:
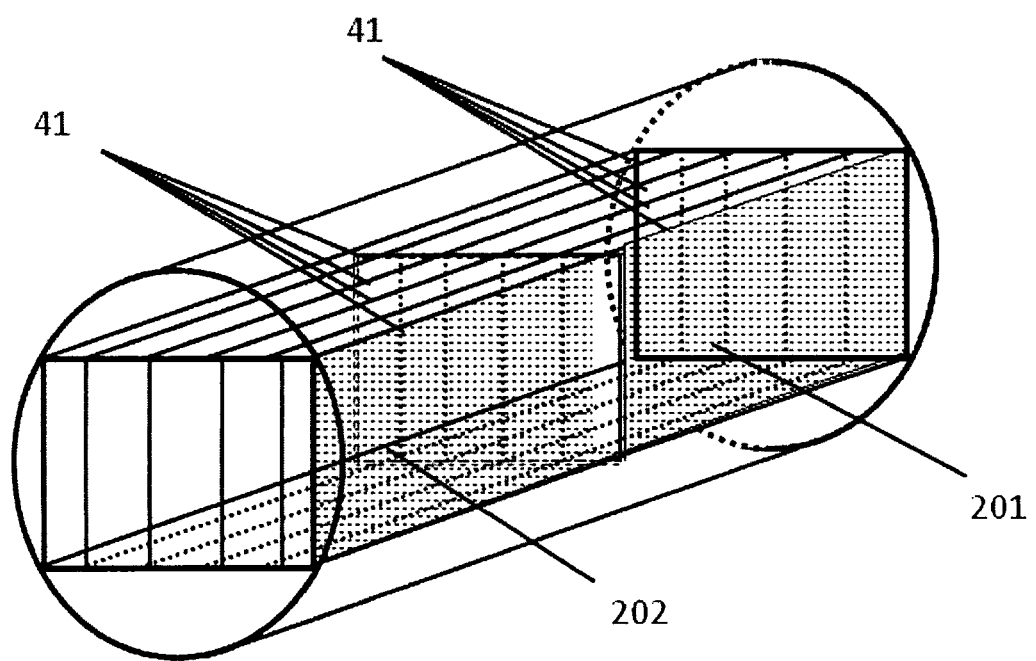
FIG. 4 schematically shows a reactor to be used in the process of the present invention, which contains thermoplates that are horizontally arranged.

FIG. 4 schematically shows a preferred reactor for use as first or second reactor, preferably as first and second reactor, in the process of the present invention. The reactor contains thermoplates 41 which are horizontally aligned forming modules, and the two modules of the reactor, module 201 and module 202, can be seen.

Figure 5:
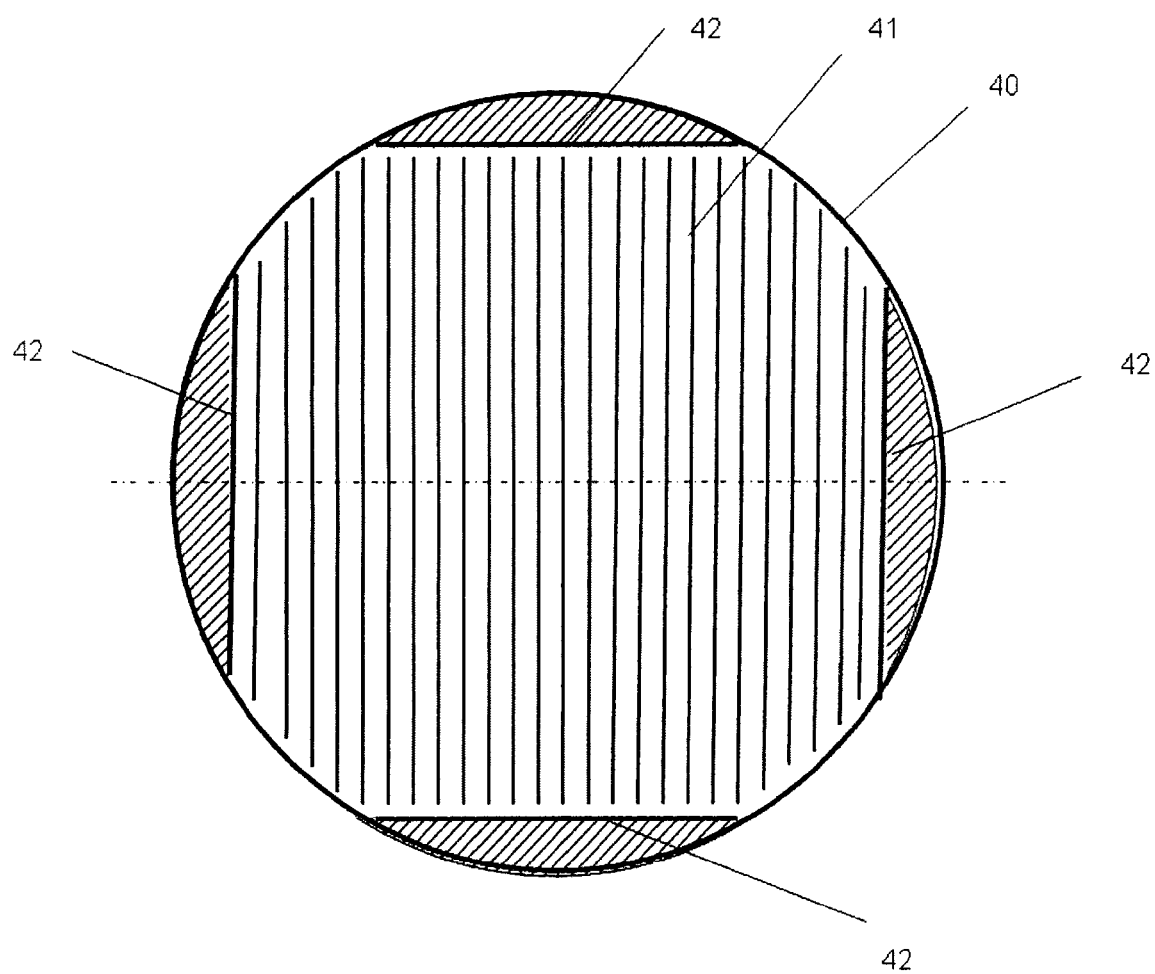
FIG. 5 schematically shows the arrangement of thermoplates in a vertical reactor.

FIG. 5 schematically shows the arrangement of thermoplates in a vertical reactor. The cylindrical outer wall 40 encompasses the thermoplates 41 and the void spaces 42. The thermoplates 41 are partially adjusted to the cylindrical wall 40. The catalyst is between the thermoplates 41.

The invention claimed is:

1. A process for the removal of hydrogen sulfide from a gas stream containing hydrogen sulfide by catalytic direct oxidation, which process comprises
   a) mixing a gas stream containing hydrogen sulfide with an oxygen containing gas to obtain a gas stream containing both hydrogen sulfide and oxygen,
   b) transferring the gas stream containing both hydrogen sulfide and oxygen into a first section of a first reactor, which first section contains a non-cooled adiabatic bed containing a first catalyst which catalyzes the oxidation of hydrogen sulfide with oxygen and the oxidation of hydrogen sulfide with sulfur dioxide, wherein the temperature of the adiabatic bed is $T_1$,
   c) transferring the gas stream from the first section of the first reactor to a second section of the first reactor, which second section contains a second catalyst which is different from the first catalyst and which second section is kept at a temperature $T_2$ wherein $T_2 \leq T_1$ and $T_2$ is higher than the dew point temperature of elemental sulfur and not higher than 300° C. whereby a gas stream depleted in hydrogen sulfide is obtained,
   d) transferring the gas stream depleted in hydrogen sulfide to a sulfur condenser to obtain a gas stream depleted in sulfur,
   e) transferring the gas stream depleted in sulfur into the first section of a second reactor, which first section contains the same catalyst as the first section of the first reactor, wherein the first section of the second reactor is kept at a temperature that is above the dew point of the elemental sulfur so that in the first section of the second reactor no elemental sulfur precipitates as liquid or solid on the catalyst,
   f) transferring the gas stream from the first section of the second reactor to the second section of the second reactor which contains the same catalyst as the second section of first reactor and which second section is kept at a temperature that is at or below the dew point of elemental sulfur so that in the second section of the second reactor elemental sulfur precipitates as liquid or solid on the catalyst,
   g) removing the desulfurized gas stream from the second reactor and
   h) after a defined time switching the operation conditions of the first reactor and the second reactor and switching the gas flow simultaneously so that the previous second reactor becomes the new first reactor and the previous first reactor becomes the new second reactor,
   i) wherein the gas stream containing hydrogen sulfide that is introduced into the first reactor has not previously been subjected to the combustion step of a Claus process, and j) wherein the temperature of the first section of the first reactor is in the range of 180 to 300° C.

2. Process according to claim 1 wherein the catalyst in the first section of the first and second reactor is selected from titanium oxide, cobalt molybdenum, nickel molybdenum and iron.

3. Process according to claim 1 wherein the catalyst in the second section of the first and second reactor is selected from aluminum oxide or activated aluminum oxide, e.g. by Ni addition.

4. Process according to claim 1, wherein the first reactor and the second reactor comprise thermoplates in the second section of the corresponding reactor.

5. Process according to claim 1, wherein the temperature in the first section of the second reactor is between 160 to 260° C.

6. Process according to claim 1, wherein the gas stream containing hydrogen sulfide and oxygen that is transferred into the first section of the first reactor also contains hydrogen.

7. Process according to claim 1, wherein the gas stream containing hydrogen sulfide is hydrogen gas, biogas, or a gas containing hydrocarbons, each of the above optionally in combination with one or more of an inert gas, nitrogen and carbon dioxide.

8. Process according to claim 1, wherein the gas stream containing hydrogen sulfide contains up to 4 vol.-% of hydrogen sulfide.

9. Process according to claim 1, wherein the gas stream containing hydrogen sulfide contains 3 vol.-% to 100 vol.-%.

10. Process according to claim 9, wherein part of the desulfurized gas stream of step g) is recycled to the first section of the first reactor.

11. Process according to claim 9, wherein an oxygen-containing gas is introduced both in the first reactor and in the second reactor.

12. Process according to claim 1, wherein the gas stream containing hydrogen sulfide and oxygen that is introduced into the first reactor has a pressure in the range of 1 bar absolute to 70 bar absolute.

13. Process according to claim 1, wherein the switching of the gas flows in step h) is effected by a distributor, comprising a housing with at least a first, a second, a third and fourth opening and a barrier element, wherein at least two spaces are provided within the housing between the barrier element and the housing, and the barrier element can be rotated around an axis of rotation between a first position and a second position such that in the first and in the second position there is a fluid connection between at least two openings of the housing and one of the spaces such that one of the spaces provides a fluid connection between the two openings of the housing, and wherein at least one of the spaces contains at least one leading element between the barrier element and the housing.

14. Process according to claim 1, wherein the sulfur recovery efficiency is at least 99%.

\* \* \* \* \*